United States Patent [19]
Wajid et al.

[11] Patent Number: 5,768,937
[45] Date of Patent: Jun. 23, 1998

[54] ACOUSTIC SENSOR FOR IN-LINE CONTINUOUS MONITORING OF GASSES

[75] Inventors: Abdul Wajid, Syracuse; Clarence Hurd, Baldwinsville; Melvin C. Hetzel, Syracuse, all of N.Y.

[73] Assignee: Leybold Inficon, Inc., E. Syracuse, N.Y.

[21] Appl. No.: 748,599

[22] Filed: Nov. 13, 1996

[51] Int. Cl.[6] .............................. G01F 17/00; G01N 29/22
[52] U.S. Cl. ................... 73/24.06; 73/24.01; 73/23.2; 73/579; 73/597; 73/648
[58] Field of Search ................ 73/24.06, 24.01, 73/23.2, 597, 579, 599, 602, 648, 646, 61.45, 24.05, 61.49

[56] References Cited

U.S. PATENT DOCUMENTS

| | | | |
|---|---|---|---|
| 2,775,885 | 1/1957 | Rassweiler et al. | 73/24 |
| 3,353,400 | 11/1967 | Schafft | 73/24 |
| 4,144,768 | 3/1979 | Andersson et al. | 73/646 |
| 4,520,654 | 6/1985 | Terhume | 73/24 |
| 4,663,977 | 5/1987 | Vander Heyden | 73/861.27 |
| 5,060,506 | 10/1991 | Douglas | 73/24.01 |
| 5,060,507 | 10/1991 | Urmson et al. | 73/24.01 |
| 5,141,331 | 8/1992 | Oehler et al. | 374/118 |
| 5,159,843 | 11/1992 | Shakkottai et al. | 73/24.05 |
| 5,247,826 | 9/1993 | Frola et al. | 73/24.01 |
| 5,313,820 | 5/1994 | Aylsworth | 73/24.01 |
| 5,351,522 | 10/1994 | Lura | 73/24.01 |
| 5,392,635 | 2/1995 | Cadet et al. | 73/24.01 |
| 5,437,194 | 8/1995 | Lynnworth | 73/861.27 |
| 5,528,924 | 6/1996 | Wajid et al. | 73/24.06 |
| 5,533,389 | 7/1996 | Kamen et al. | 73/149 |
| 5,627,323 | 5/1997 | Stern | 73/861.28 |

*Primary Examiner*—Hezron E. Williams
*Assistant Examiner*—J. David Wiggins
*Attorney, Agent, or Firm*—Wall Marjama & Bilinski

[57] ABSTRACT

An acoustic cell includes multiple acoustic cavities fluidly coupled together. At least two of the acoustic cavities have unequal lengths and cross sections. End segments of the acoustic cell are uniformly cylindrically shaped or conically shaped. A driver transducer at one end of the acoustic cell and a receiver transducer at another end of the acoustic cell are acoustically isolated from the acoustic cell. A pair of preferably metallic isolation diaphragms transmit acoustic signals to and from the transducers without significantly altering the phase-frequency characteristics of the acoustic signals. The acoustic cell operates as an acoustic resonator operating at frequencies lower than any possible self-resonance frequencies of the isolation diaphragms or the driver and receiver transducers. When a binary gas is flowed through the cell, a processor detects a resonant frequency of the gas within the cell to determine a composition of the gas.

22 Claims, 10 Drawing Sheets

ACOUSTIC SENSOR FOR IN-LINE CONTINUOUS MONITORING OF GASSES

BACKGROUND OF THE INVENTION

This invention relates to a high speed, high sensitivity acoustic cell, and in particular, to an acoustic cell suitable for in-line continuous monitoring of MOCVD precursor gasses.

There has been steadily growing interest in the Metalorganic Chemical Vapor Deposition (MOCVD) processes, particularly for growing complex thin film structures such as, for example, InGaAsP devices for opto-electronic applications. When forming the devices, film growth takes place in a cold wall reactor in which the reactants are introduced in precise amounts in a controlled manner. The quality and reproducibility of the devices critically depend on precise delivery of the precursor reagents into the reactor.

The precursor reagents are typically delivered into the reactor from a solid, such as trimethylindium (Tmi), or liquid, such as trimethylgallium (TMG), source by flowing a carrier gas such as hydrogen. A concentration of the precursor reagent is typically estimated from the knowledge of mass flow rates, partial pressure of the source, and the operating pressure. Conventional assumptions are that the vapor pressure of the source is constant and that the mole fraction of the precursor in the carrier gas remains steady. These assumptions are not always valid if the source's vapor pressure is low, as is the case with a solid source, or if the source has been extensively used. Although there are many ways to examine the quality of the thin film after it is formed, it is preferable from a quality control and process control standpoint to monitor and control the consistency of the precursor reagents before the film begins growing.

Monitoring the consistency of a precursor reagent in vapor form is accomplished by measuring the proportion of the precursor reagent in the carrier gas. This binary gas analysis is usually accomplished using optical, chemical, or acoustic techniques. Examples of acoustic techniques are the timeof-flight technique and the resonant cavity technique. In a time-of-flight device, tuned ultrasonic transducers are used to send and detect short (5 $\mu$s) bursts of acoustic pulses. The sonic speed is measured which directly relates to the composition of the binary gas. Operating frequencies are usually around 100 kHz or more. Typical problems with time-of-flight devices include imprecise pulse shaping, echoes, parasitic conduction, signal attenuation, and pulse shape distortion. These problems limit the performance of time-of-flight devices when used with hydrogen-type gasses at low pressures.

Resonant cavity devices measure the resonant frequency of the binary gas mixture. The resonant frequency directly relates to the composition of the binary gas. Problems with ultrasonic resonant cavity devices arise for several reasons. First, broadly tuned transducers are used to cover the range of operating frequencies. A resonant cavity device thus has to be designed for a specific gas, thereby being limited in its application. Second, when operating at frequencies of tens to hundreds of kilohertz, many competing modes of resonance, such as radial, axial, and azimuthal, exist within the sensor. These resonances couple with overtone resonances of individual components, such as, for example, diaphragms. Identifying which resonance is strictly due to the test gas and tracking that resonance despite fluctuations in composition, temperature, and pressure is very difficult. Third, the existence of intrinsic thermo-elastic attenuation, that is, the intrinsic energy loss of sound waves, in the gas medium causes problems. In hydrogen type gasses, the attenuation increases as the square of the operating frequency, thus making the cavity resonance technique unattractive in the ultrasonic range.

Based on the above, design considerations include low volume and frequency. The sensor volume is directly related to the time it takes to sweep the sensor at a given gas flow rate. If fast response is required from the sensor, its volume must be as small as practical. However, there is a significant drawback to reducing the volume when using hydrogen gas. Since hydrogen is a very light gas, there is little fluid medium to establish standing waves in the enclosed volume when the operating pressure is below 100 Torr (10% of atmospheric pressure). A parasitic signal traveling through a metal enclosure of the resonator device becomes comparable to or dominant over the signal traveling through the gas, thereby distorting the phase-frequency relationship. The quality factor (Q) of the resonator deteriorates significantly making it difficult to maintain stable resonance. Maintaining the Q at the highest possible level is very important to avoid loss of steady-state stability, which causes reduced sensitivity as a binary gas analyzer. A low volume, less than 20 cc, and a high Q, greater than 20, are thus desirable.

The operating frequency depends in part on the length of the sensor cell, which in turn depends on the volume and desired Q. For an end diameter of one inch (to fit an INCONEL 1" diaphragm developed by the assignee) for a right circular cylinder sensor cell, the cell's length is 35.5 mm for a volume of 18 cc. When used with hydrogen gas (speed of sound of 1260 m/s), the lowest operating frequency attainable is approximately 17,735 Hz. Keeping the volume constant, one could design a smaller diameter but longer length, thereby obtaining a lower resonant frequency. However, since acoustic signal transmission through a diaphragm varies as the fourth power of its diameter, any reduction in diaphragm size is avoided.

There are many problems associated with a 17 KHz resonator. For example, most microphones have relatively flat response up to 7 KHz. Beyond 10 KHz, microphone efficiency drops off drastically except at frequencies where the microphone self-resonates. The INCONEL diaphragms developed by the assignee have their lowest mode frequency in the range of 5.5–7 KHz. It is preferable to operate below this range to avoid complications from internal diaphragm resonances. Finally, internal friction increases as the square of the operating frequency in hydrogen type gasses.

OBJECTS AND SUMMARY OF THE INVENTION

It is therefore an object of the present invention to provide an acoustic sensor that overcomes the drawbacks and limitations of the prior art.

It is another object of the invention to provide an acoustic sensor that has a low volume, a high Q, and an operating frequency under 5 KHz.

It is a further object of the invention to provide an acoustic sensor capable of determining binary gas composition without the need for factory calibration.

It is a still further object of the invention to provide an acoustic sensor that reduces parasitic signal conductance.

It is yet a further object of the invention to provide an acoustic sensor that enhances a signal-to-noise ratio at very low pressures.

Briefly stated, an acoustic cell includes multiple acoustic cavities fluidly coupled together. At least two of the acoustic cavities have unequal lengths and cross sections. End segments of the acoustic cell are uniformly cylindrically shaped or conically shaped. A driver transducer at one end of the acoustic cell and a receiver transducer at another end of the acoustic cell are acoustically isolated from the acoustic cell. A pair of preferably metallic isolation diaphragms transmit acoustic signals to and from the transducers without significantly altering the phase-frequency characteristics of the acoustic signals. The acoustic cell operates as an acoustic resonator operating at frequencies lower than any possible self-resonance frequencies of the isolation diaphragms or the driver and receiver transducers. When a binary gas is flowed through the cell, a processor detects a resonant frequency of the gas within the cell to determine a composition of the gas.

According to an embodiment of the invention, an acoustic cell includes a cell housing, said cell housing including a plurality of acoustic cavities, flowing means, fluidly connected to said cell housing, for flowing a gas through said cell housing, driving means at a first end of said cell housing for sending an acoustic signal through said gas flowing through said cell housing, and receiving means at a second end of said cell housing for receiving said acoustic signal.

According to an embodiment of the invention, an acoustic sensor includes a housing, said housing including a plurality of acoustic cavities, flowing means, fluidly connected to said housing, for flowing a gas through said housing, driver transducing means at a first end of said housing for receiving a driving electrical signal, converting said driving electrical signal to a driving acoustic signal, and sending said driving acoustic signal through said gas flowing through said housing, receiver transducing means at a second end of said housing for receiving a received acoustic signal, converting said received acoustic signal to a received electrical signal, and outputting said received electrical signal, processing means for sending said driving electrical signal to said driver transducing means and for receiving said received electrical signal outputted by said receiver transducing means, means for varying a frequency of said driving acoustic signal, means for detecting a resonance frequency associated with said gas, and said processing means including means for determining a composition of said gas.

According to an embodiment of the invention, a method for determining a composition of a binary gas includes the steps of providing an acoustic cell having a plurality of acoustic cavities, flowing a gas through said acoustic cell, receiving a driving electrical signal from a digital signal controller, converting said driving electrical signal to a driving acoustic signal, sending said driving acoustic signal through said gas flowing through said acoustic cell, receiving a received acoustic signal after the step of sending said driving signal through said gas, converting said received acoustic signal to a received electrical signal, outputting said received electrical signal to said digital signal controller, processing, within said digital signal controller, said received electrical signal to detect a resonance frequency associated with said gas, and determining, based on said resonance frequency, said composition of said gas.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

An analysis of the composition of a gas is achieved by measuring the, speed of sound in a given gas media. For a binary mixture of gasses, the speed of sound c is given by $$c^2 = \bar{\gamma} \frac{RT}{\bar{M}} \quad (1)$$

where $\bar{\gamma}$ is the average specific heat ratio of the gas mix, $\bar{M}$ is the number average molecular weight of the gas mix, R is 8311.7 inks units (the universal gas constant), and T is the temperature in degrees Kelvin.

If the mole-fraction of precursor gas in a carrier gas is x, then $$\frac{1}{\bar{\gamma}-1} = \frac{x}{\gamma_1-1} + \frac{1-x}{\gamma_2-1} \quad (2)$$

which can be rewritten as $$\bar{\gamma} = 1 + \frac{(\gamma_1-1)(\gamma_2-1)}{x(\gamma_2-1)+(1-x)(\gamma_1-1)} \quad (3)$$

and $$\bar{M} = xM_1 + (1-x)M_2 \quad (4)$$

where the subscripts 1 and 2 denote the precursor gas and carrier gas, respectively. The mole fraction information for a given binary gas is obtained from equations (1)–(4) as follows. For convenience, the following quantities are defined:

$$m = \frac{M_1}{M_2}, \quad (5)$$

$$g = \frac{\gamma_1}{\gamma_2}, \text{ and} \quad (6)$$

$$h = \frac{1}{\gamma_2}. \quad (7)$$

Combining equations (5)–(7) with equations (1)–(4), we obtain $$\bar{M} = M_2((m-1)x + 1) \quad (8)$$

and $$\bar{\gamma} = 1 + \gamma_2 \frac{(g-h)(1-h)}{x(1-g)+(g-h)}. \quad (9)$$

Using equations (8) and (9) with equation (1), we obtain $$c^2 = c_2^2 \frac{h + \frac{(g-h)(1-h)}{x(1-g)+(g-h)}}{1+(m-1)x} \quad (10)$$

where $c_2$ is the speed of sound in the pure carrier gas as given by $$c_2 = \sqrt{\frac{\gamma_2 RT}{M_2}}. \quad (11)$$

Since the measured resonance frequencies in an acoustic resonator are directly proportional to the speed of sound, we define the ratio $$\lambda = \left(\frac{c}{c_2}\right)^2 = \left(\frac{f}{f_2}\right)^2 \quad (12)$$

where $f$ and $f_2$ are the resonant frequencies in the mixed gas and the pure carrier gas respectively. Combining equations. (10)–(12), we obtain $$\lambda(1+(m-1)x) = h + \frac{(g-h)(1-h)}{x(1-g)+(g-h)}. \quad (13)$$

Simplifying equation (13) leads to a quadratic equation in the form $$Ax^2 + Bx + C = 0 \quad (14)$$

where $$A = \lambda(m-1)(1-g), \quad (15)$$

$$B = \lambda m(g-h) + \lambda(1-2g+h) - h(1-g), \text{ and} \quad (16)$$

$$C = (\lambda-1)(g-h) \quad (17)$$

The solutions to equation (14) are in the form $$x_{1,2} = \frac{-B \pm \sqrt{B^2 - 4AC}}{2A}. \quad (18)$$

Figure 1:
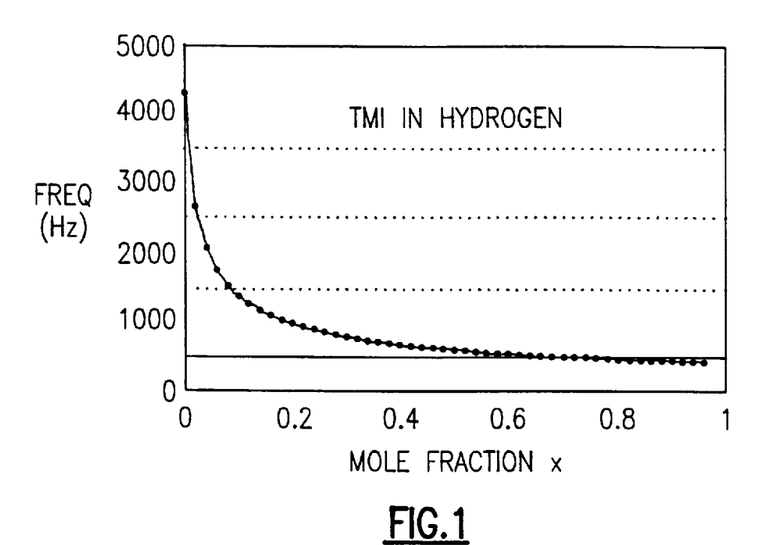
FIG. 1 shows a monotonic relationship between mole-fraction and the speed of sound in a medium.

Acceptable solutions must stay within realistic bounds such that $0 \leq x_{1,2} \leq 1$. In the overwhelming majority of binary gas systems, there is only one solution for x, thus implying a monotonic relationship between the mole-fraction of the precursor gas and the speed of sound. FIG. 1 shows this relationship for TMI in hydrogen carrier gas.

In this invention, the variables m, g, and i in equation (13) are known for the binary gasses being analyzed: Once $\lambda$ is determined, $x_{1,2}$ can be computed. From equation (12), since we know $f_2$, we can compute $\lambda$ once we determine f. The following discussion of acoustic resonance frequencies is helpful in understanding the invention.

A gas resonator can be viewed as a harmonic force driven damped resonator governed by $$m\frac{d^2x}{dt^2} + 2\lambda\frac{dx}{dt} + kx = A_0\cos(2\pi ft) \quad (19)$$

where m is the mass of the resonator, $\lambda$ is the damping coefficient (logarithmic decrement), k is the spring constant, $A_0$ is the amplitude of the driving force, f is the frequency of the driving force, and x is the instantaneous displacement of the mass at time t. The solution for x is in the form $x = x_0 \cos(2ft+\omega)$ where $x_0$ and $\omega$ respectively denote the amplitude of oscillation at the driving frequency and the phase lag between the force and resulting mass displacement x. It is known that $x_0$ can be expressed as $$x_0 = \frac{(A_0/2\pi m)}{\sqrt{(f_0^2 - f^2)^2 + (ff_0/Q)^2}} \quad (20)$$

where $f_0$ is the resonant frequency given by $$f_0 = \frac{1}{2\pi}\sqrt{\frac{k}{m}} \quad (21)$$

and Q is the quality factor of the resonator given by $$Q = \pi f_0 m/\lambda. \quad (22)$$

The phase lag is obtained from $$\tan\phi = \frac{-ff_0}{Q(f_0^2 - f^2)}. \quad (23)$$

Thus, amplitude of oscillation $x_0$ and phase lag $\omega$ completely describe the system under consideration. The amplitude of oscillation $x_0$ peaks when driving frequency f equals $f_0$. Analysis of equation (23) shows that $\omega = 0$ for $f \ll f_0$, $\omega = -\pi/2$ for $f = f_0$, and $\omega = -\pi$ for $f \gg f_0$.

Since $Q^{-1}$ represents the ratio of the rate of energy loss due to damping compared to the total energy stored in the resonator, $f_0$ and Q adequately characterize the mechanics of the resonator system.

Figure 2:
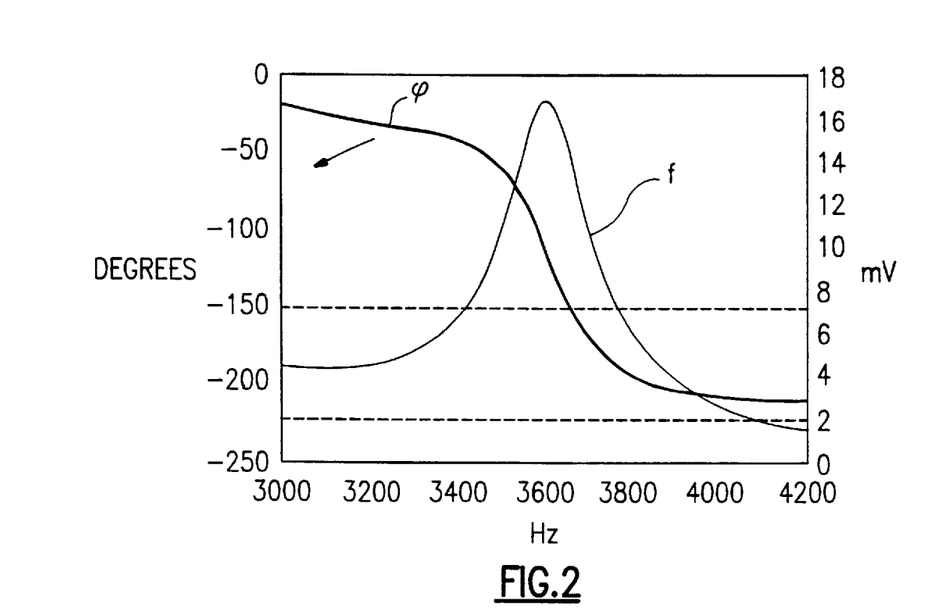
FIG. 2 shows typical phase and amplitude variations in the vicinity of a resonance.

FIG. 2 shows typical phase and amplitude variations in the vicinity of a resonance.

To determine the resonance frequency $f_0$ from amplitude measurements, we define from equation (20)

$$y(f) = \frac{1}{x_0^2} = \left(\frac{2\pi m}{A_0}\right)^2 ((f_0^2 - f^2)^2 + (ff_0/Q)^2). \quad (24)$$

Dividing y(f) by $y(f_0)$, we obtain $$\frac{y(f)}{y(f_0)} = \frac{(f_0^2 - f^2)^2 + (ff_0/Q)^2}{(f_0^2/Q)^2}. \quad (25)$$

In the vicinity of the resonance, $f_0^2 - f^2 \approx 2f_0(f_0 - f)$. Since $f_0$ is not yet determined, we define frequencies with respect to a reference frequency $f_R$ in the neighborhood of resonance frequency $f_0$ such that $$f_0 - f = (f_R - f) + (f_0 - f_R) = \Delta + \Delta_0. \quad (26)$$

Rewriting $y(f)/y(f_0)$ in terms of an incremental frequency $\Delta$, we obtain $$\frac{y(f)}{y(f_0)} = 1 + 4Q^2(f_0 - f)^2/f_0^2 = (2Q/f_0)^2(\Delta + \Delta_0)^2 + 1 \quad (27)$$

which can be written in quadratic form as $$y(\Delta) = b_0 + b_1\Delta + b_2\Delta^2 \quad (28)$$

where $$b_0 = (1 + (2Q/f_0)^2\Delta_0^2)y(f_0), \quad (29)$$

$$b_1 = 2\Delta_0(2Q/f_0)^2 y(f_0), \text{ and} \quad (30)$$

$$b_2 = (2Q/f_0)^2 y(f_0). \quad (31)$$

A number of measurements are preferably taken around $f_R$ for performing parabolic regression on $y(\Delta)$ to determine the best-fitted values of $b_0$, $b_1$, and $b_2$ as is explained later. Equations (29) through (31) then yield $$\Delta_0 = \frac{0.5 b_1}{b_2}, \quad (32)$$

$$f_O = f_R + \Delta_0, \quad (33)$$

$$Q = \frac{(f_0/2)}{\sqrt{(b_0/b_2) - \Delta_0^2}} \quad (34)$$

$$y(f_O) = b_O - b_2\Delta_0^2, \text{ and} \quad (35)$$

$$x_0(f_0) = \frac{1}{\sqrt{y(f_0)}}. \quad (36)$$

Figure 3:
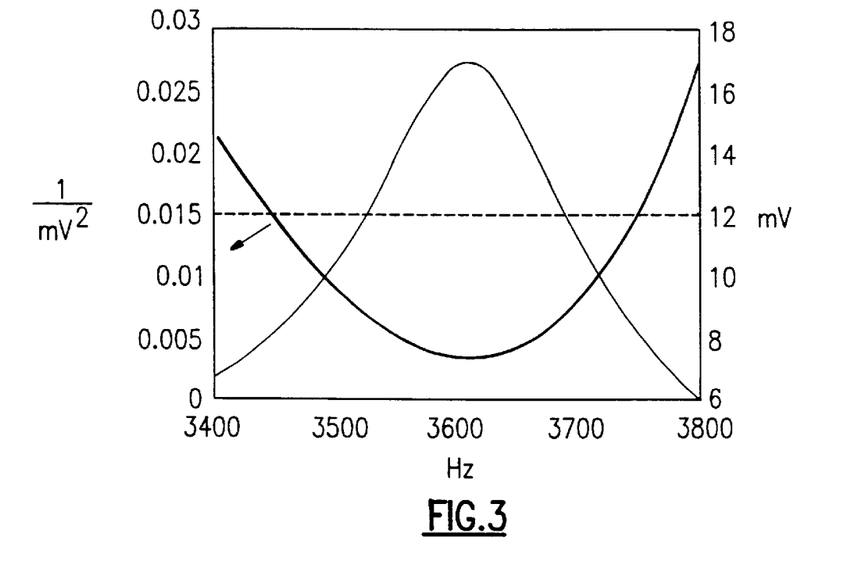
FIG. 3 shows a plot of $y(f)=1/x_0^2$ and $x_0$ in the vicinity of a resonance.

FIG. 3 shows a plot of $y(f) = 1/x_0^2$ and $x_0$ in the vicinity of a resonance.

To determine the resonance frequency $f_0$ from phase measurements, we rewrite equation (23) as $$(f_o^2 - f^2)\tan\phi = -ff_o/Q \text{ and} \quad (37)$$

$$\frac{\partial\phi}{\partial f} = \frac{-(f_0/Q)(f_0^2 + f^2)}{(f_0^2 - f^2)^2 + (ff_0/Q)^2}. \quad (38)$$

As noted above, $f_0^2 - f^2 \approx 2f_0(f_0 - f)$ in the vicinity of the resonance. Therefore, $$\frac{\partial\phi}{\partial f} \approx \frac{-2f_0^2(f_0/Q)}{4f_0^2(f_0 - f)^2 + (ff_0/Q)^2}. \quad (39)$$

Again, since $f_0$ is not yet determined, we define frequencies with respect to a reference frequency $f_R$ in the neighborhood of resonance frequency $f_0$ such that $f_0 - f = (f_R - f) + (f_0 - f_R) = \Delta + _0 + tm$ (40)

Therefore, $$\frac{\partial\phi}{\partial f} = -\frac{\partial\phi}{\partial\Delta} \quad (41)$$

and $$y(\Delta) = \frac{\partial\Delta}{\partial\phi} \approx (2Q/f_0)(\Delta + \Delta_0)^2 + (f_0/2Q) = b_0 + b_1\Delta + b_2\Delta^2 \quad (42)$$

where $$b_0 = (f_0/2Q) + (2Q/f_0)\Delta_0^2, \quad (43)$$

$$b_1 = (2Q/f_0)2\Delta_0, \text{ and} \quad (44)$$

and $$b_2 = (2Q/f_0). \quad (45)$$

A number of measurements are taken around $f_R$ before performing parabolic regression to determine the best fitting regression coefficients. Equations (43)–(45) then yield $$\Delta_0 = \frac{0.5 b_1}{b_2}, \quad (46)$$

$$f_O = f_R + \Delta_0, \text{ and} \quad (47)$$

$$Q = \frac{(f_0/2)}{\sqrt{b_0/b_2 - \Delta_0^2}}. \quad (48)$$

Figure 4:
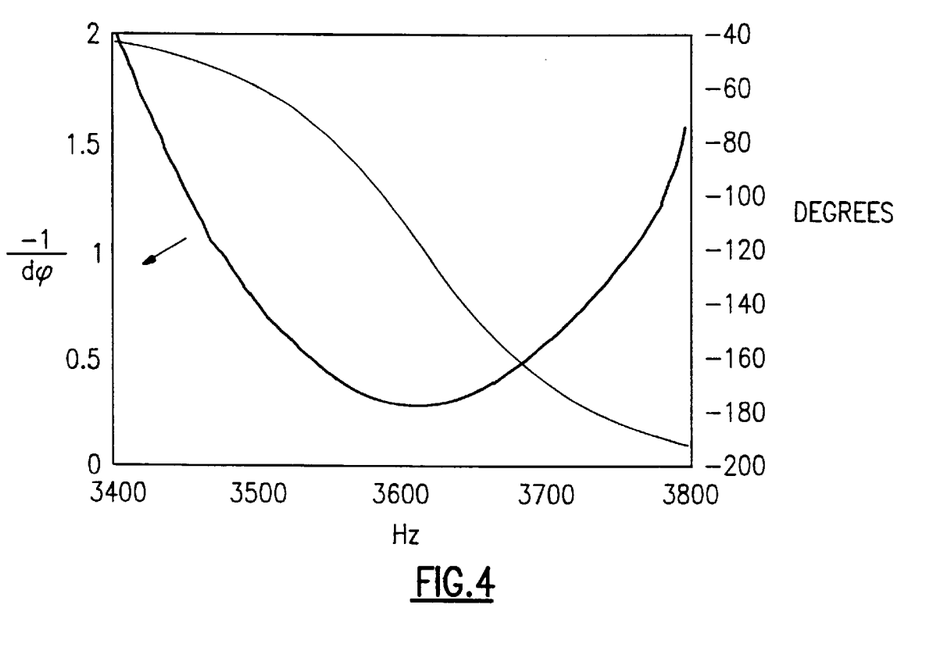
FIG. 4 shows a plot of $-1/d\omega$ and $\omega$ in the vicinity of a resonance.

FIG. 4 shows a plot of $-1/d\omega$ and $\omega$ in the vicinity of a resonance.

The parabolic regression method previously referred to is explained as follows. With a model in the form of $$y(x) = b_0 + b_1 x + b_2 x^2 \quad (49)$$

the regression equations can be constructed in matrix form as $$\begin{bmatrix} \Sigma Y \\ \Sigma xY \\ \Sigma x^2 Y \end{bmatrix} = \begin{bmatrix} n & \Sigma x & \Sigma x^2 \\ \Sigma x & \Sigma x^2 & \Sigma x^3 \\ \Sigma x^2 & \Sigma x^3 & \Sigma x^4 \end{bmatrix} * \begin{bmatrix} b_0 \\ b_1 \\ b_2 \end{bmatrix} \quad (50)$$

The best fitted parameters are obtained by inverting this regression matrix. Although this matrix can be inverted for any arbitrary number of measured data points, the task is simplified by choosing data points which are equi-spaced and taken symmetrically about a reference zero. Half of the elements in the matrix reduce to zero. For example, if 11 data points 1 Hz apart are taken around the reference point, then $n = 11$, $\Sigma = 0$, $\Sigma x^2 110$, $\Sigma x^3 = 0$, and $\Sigma x^4 = 1958$. With these values, the b values are obtained from the following inverted matrix equation $$\begin{bmatrix} b_0 \\ b_1 \\ b_2 \end{bmatrix} = \begin{bmatrix} 1958/9438 & 0 & -110/9438 \\ 0 & 1/110 & 0 \\ -110/9438 & 0 & 11/9438 \end{bmatrix} * \begin{bmatrix} \Sigma Y \\ \Sigma xY \\ \Sigma x^2 Y \end{bmatrix} \quad (51)$$

Once the b parameters are known the resonant frequency $f_0$ is determined from amplitude measurements or phase measurements as described above. If the data points are equi-spaced but not necessarily 1 Hz apart, the b parameters need to be scaled by an incremental step s as follows:

$b_0 \rightarrow b_0$, $b_1 \rightarrow b_1/s$, and $b_2 \rightarrow b_2/s^2$.

Figure 5:
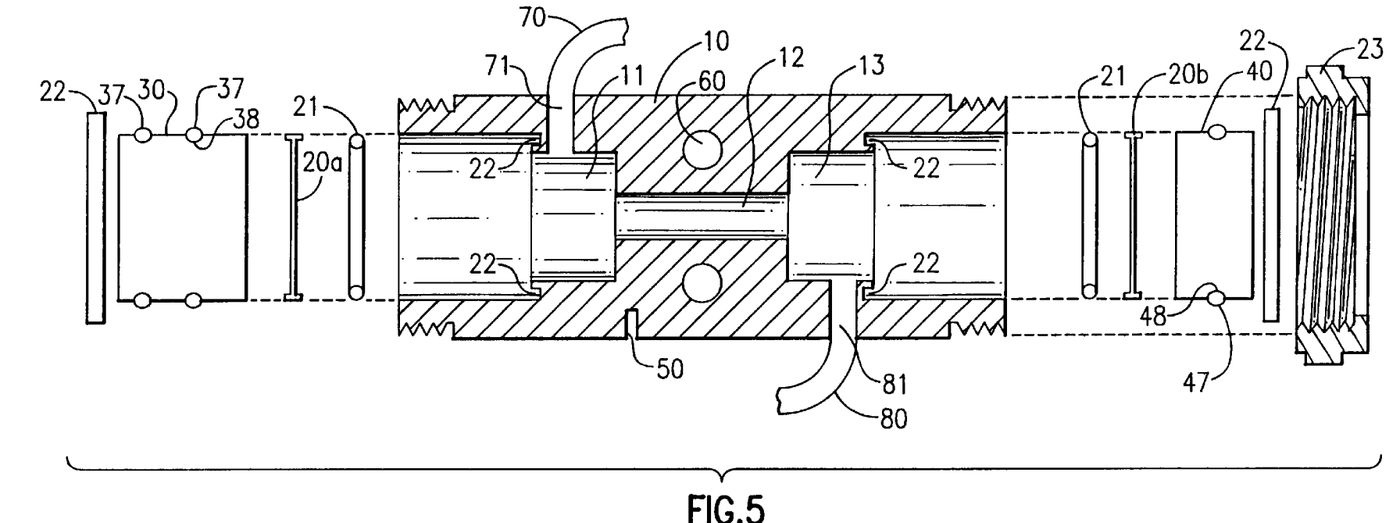
FIG. 5 shows a cross section of an acoustic cell according to an embodiment of the present invention.
Figure 6A:
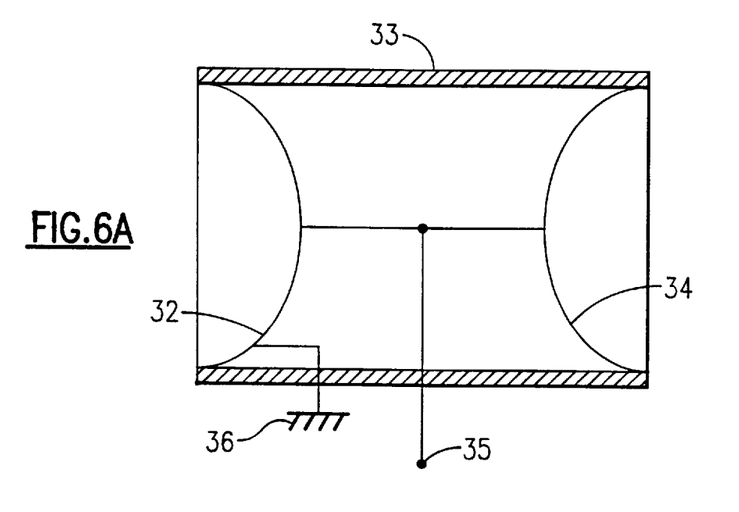
FIG. 6A shows a metal housing for a driver microphone and an anti-driver microphone according to an embodiment of the present invention.
Figure 6B:
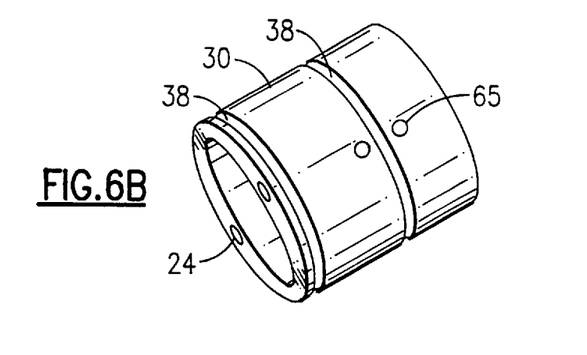
FIG. 6B shows a driver microphone cartridge according to an embodiment of the present invention.
Figure 7:
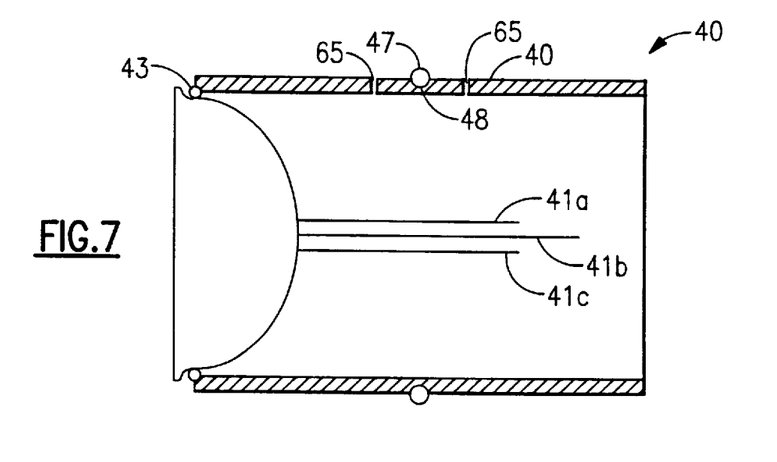
FIG. 7 shows a receiver microphone cartridge according to an embodiment of the present invention.

Referring to FIGS. 5–7, an acoustic cell 1 includes a housing 10 preferably made of metal. Housing 10 includes a plurality of acoustic cavities, 5 such as, for example, acoustic cavities 11, 12, and 13. Acoustic cavity 12 is smaller than acoustic cavities 11 and 13. First and second diaphragms 20a, 20b are preferably of metal such as INCONEL, stainless steel, or other nonoxidizing metal alloy. When first and second diaphragms 20a, 20b are installed in housing 10, a sealing o-ring 21 fits into an o-ring groove 22 in housing 10. First and second diaphragms 20a, 20b thus form a side wall of acoustic cavities 11 and 13.

Referring to FIGS. 6A and 6B, a driver transducer such as, for example, a driver microphone cartridge 30 fits into housing 10 abutting first diaphragm 20a. Driver microphone cartridge 33 includes a metal housing 30 which contains a driving microphone 34 for driving first diaphragm 20a and an anti-driving microphone 32. Driving microphone 34 and anti-driving microphone 32 are preferably epoxied to housing 33. Housing 33 is preferably acoustically isolated from driver microphone cartridge 30 by two isolation o-rings (not shown) in an inner cylindrical wall of driver microphone cartridge 30. Two isolation o-ring grooves 38 in an outer cylindrical wall of driver microphone cartridge 30 allow two o-rings 37 to acoustically dampen driver microphone cartridge 30, thereby substantially reducing any signal transmittance through a parasitic path going through housing 10. Electrodynamic microphones are satisfactory as driver transducers in the 1–7 KHz range. Two vent holes 65, one on either side of o-ring groove 38, equalize pressure variations within driver microphone cartridge 30.

Driver microphone cartridge 30 includes an end washer 22 for holding housing 33 in place within driver microphone cartridge 30. End washer 22 is preferably fastened to driver microphone cartridge 30 via screws (not shown) fitting into screw holes 24 as shown in FIG. 6B. An isolation o-ring (not shown) preferably fits between end washer 22 and housing 33. Driver microphone cartridge 30 is held in place in housing 10 by a collar 23.

A driving input 35 activates driving microphone 34 and anti-driving microphone 32 synchronously so that driver microphone cartridge 30 transfers minimal momentum to housing 10 while transmitting an acoustic signal through a gas medium in Acoustic cell 1. Thus the signal transmittance through the parasitic path is nearly zero, whereas the signal transmittance through the gas medium is undiminished. Driving microphone 34 and anti-driving microphone 32 are optionally individually adjustable for phase and amplitude. The microphones are sufficiently matched in phase and amplitude if manufactured by the same manufacturer with standard commercial tolerances.

Referring to FIG. 7, a receiver transducer such as, for example, receiver microphone cartridge 40 fits into housing 10 abutting second diaphragm 20b. Receiver microphone cartridge 40 includes a receiver microphone 42 for receiving vibrations from second diaphragm 20b and outputting a received signal 41a. Receiver microphone 42 is preferably an electret type microphone due to the very high sensitivity and fairly flat frequency response when detecting acoustic signals. Due to its small size, receiver microphone 42 fits directly into receiver microphone cartridge 40. Receiver microphone 42 is preferably acoustically isolated from receiver microphone cartridge 40 by an isolation o-ring 43. Receiver microphone cartridge 40 is acoustically isolated from housing 10 by an isolation o-ring 47 fitted into an o-ring groove 48. Two vent holes 65, one on either side of o-ring groove 38, equalize pressure differences within receiver microphone cartridge 40. Received signal 41a, a power wire 41b, and a ground wire 41c are all electrically isolated from receiver microphone cartridge 40.

Receiver microphone 42, driving microphone 34, and anti-driving microphone 32 are mounted as previously described to minimize noise conduction through the metal parts from one end of acoustic cell 1 to the other end. Mining noise conduction is significant at the low operating pressures of the present invention.

Referring back to FIG. 5, metallic diaphragms 20a, 20b are interposed between the acoustic resonator chamber, which are made up of acoustic cavities 11, 12, and 13, and driving and receiver microphones 34, 42, which have nonmetallic components, to maintain contamination free flow of the gas while protecting the microphones from potential pressure bursts within the acoustic resonator chamber. Diaphragms 20a, 20b are preferably semi-tensioned one inch diameter diaphragms with fundamental mode frequencies approximately 6 KHz at atmospheric pressure.

A gas inlet tube 70 is connected to acoustic cavity 11 via a gas inlet 71. A gas outlet tube 80 is connected to acoustic cavity 13 via a gas outlet 81. An RID temperature sensor 50, preferably platinum, is emplaced in housing 10 to provide accurate temperature information. Two heater mounting holes 60 are preferably drilled through a thick portion of housing 10 for mounting a heater element (not shown) to maintain acoustic cell 1 at a given temperature to within 0.1° C.

Figure 8:
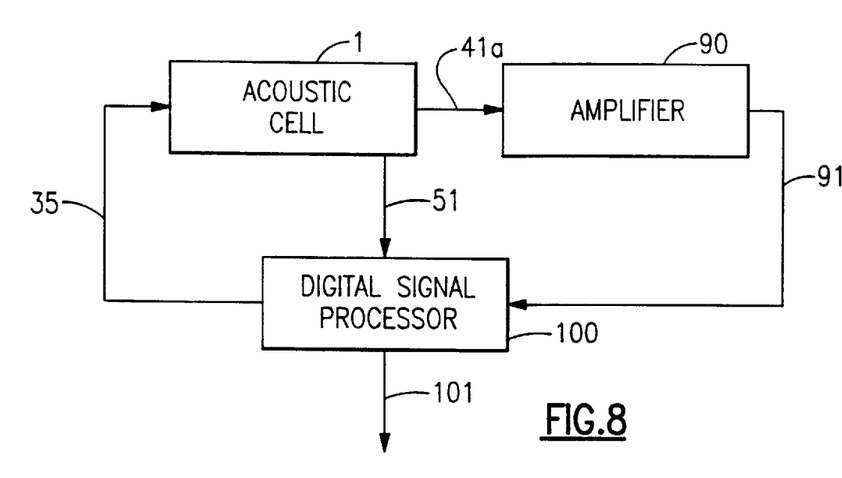
FIG. 8 shows an acoustic sensor according to an embodiment of the present invention incorporating the acoustic cell of FIG. 5.

Referring to FIG. 8, a digital signal processor 100 sends driving input 35 to acoustic cell 1. Digital signal processor 100 preferably includes a digital waveform synthesizer, such as a digital sine wave generator, for sending a synthesized sine wave 98 to a D/A converter 97 which outputs an analog sine wave 96. An amplifier 95 amplifies sine wave 96 to produce a driving input 35 for acoustic cell 1. Acoustic cell 1 outputs received signal 41a which directly relates to the composition of the gas medium within acoustic cell 1. Received signal 41a is amplified by an amplifier 90 which outputs an amplifier output signal 91 to an A/D converter 92 for sending a digital signal 93 to digital signal processor 100. Digital signal processor 100 also receives a temperature signal (not shown) from RTD temperature sensor 50 to use in its calculations. Digital signal processor 100 preferably includes a digital phase detector that compares a phase of received signal 41 with a phase of driving input 35 approximately 200 times per second. An on-board micro controller determines the average resonance frequency five times per second. Digital signal processor 100 then outputs a processor output signal 101 indicating the gas composition of the binary gas in acoustic cell 1.

An alternative measuring mode, which can be called digital phase-lock mode, is briefly described. In a given gas medium, a phase lag between the receiver and driver transducers at the resonance frequency $f_0$ remains steady unless the gas composition fluctuates. Any change in the phase lag due to gas compositional change forces the digital sine wave generator to adjust the driving frequency of driving input 35 so that the phase lag returns to its steady state value. During operation of acoustic cell 1, if the phase between driving microphone 34 and receiver microphone 42 is matched, the occurrence of a difference in phase signals a change in the composition of the gas. The frequency of driving input 35 is changed to match phase. The amount of change in frequency required to match phase provides the information necessary to determine the change in gas composition. Thus, the difference between the adjusted frequency and the steady state resonance frequency $f_0$ allows computation of the change in binary gas composition. This measuring mode is faster than the one described earlier, but is only useful in monitoring steady state processes.

Calibration occurs at the anticipated operating temperature, pressure, and flow rate by passing pure carrier gas through acoustic cell 1 and taking a baseline frequency reading. All measurements of the binary test gas are then with respect to the baseline reading. The acoustic sensor is thus free from any required factory set calibration. Of course, any drastic change in operating conditions (operating temperature, pressure, and flow rate) necessitates a new baseline measurement to maintain maximum accuracy.

Figure 9A:
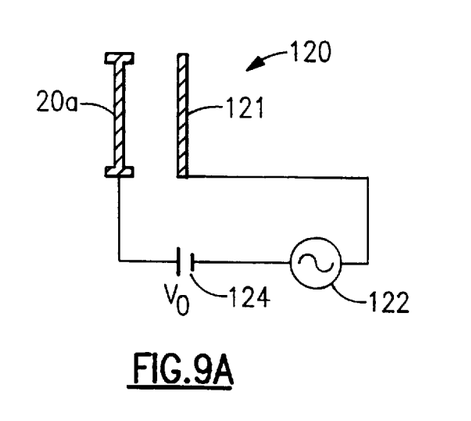
FIG. 9A shows an electrostatic drive microphone used in an embodiment of the present invention.

Referring to FIG. 9A an electrostatic drive microphone is preferably used in place of electrodynamic microphones 32, 34 in high temperature applications of the present invention. An electrostatic drive device 120 can be applied directly to first diaphragm 20a. First diaphragm 20a is driven by a sine wave generator 122 through a DC bias 124 preferably in the range of 100–500 V. Sine wave generator 122 is grounded into a ground plate 121. The force F(t) applied to diaphragm 20a can be expressed as $F(t) \approx -CV_0 u \cos \omega t$, where C is the static capacitance between diaphragm 20a and ground plate 121, $V_0$ is the DC bias 124, and u is the amplitude of driving sinewave generator 122.

Figure 9B:
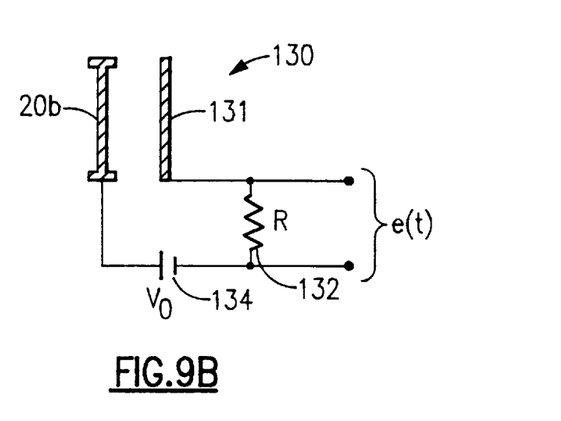
FIG. 9B shows a capacitance microphone used in an embodiment of the present invention.

Referring to FIG. 9B, a capacitance microphone 130 is preferably used in place of electret microphone 42 in high temperature applications of the present invention. A backplate 131 forms a capacitor with diaphragm 20b. A DC bias 134, preferably in the range from 20–100 V., and a 132 preferably less than 10 MΩ, allow a signal e(t) to be detected. Signal e(t) can be expressed as $$e(t) \approx RV_0 \left( \frac{\partial c}{\partial t} \right),$$

where $$\frac{\partial c}{\partial t}$$

is the temporal derivative of the capacitance between diaphragm 20b and backplate 131.

The present invention was operationally evaluated as follows. Acoustic cell 1 was typically 3.850" in length with a typical diameter of 1.750". Acoustic cavities 11 and 13 were typically 0.600" long with a typical diameter of 1.000", while acoustic cavity 12 was typically 1.200" long with a typical diameter of 0.375". Diaphragms 20a, 20b, including isolation o-rings 21, were typically 1.206" in diameter.

Figure 10:
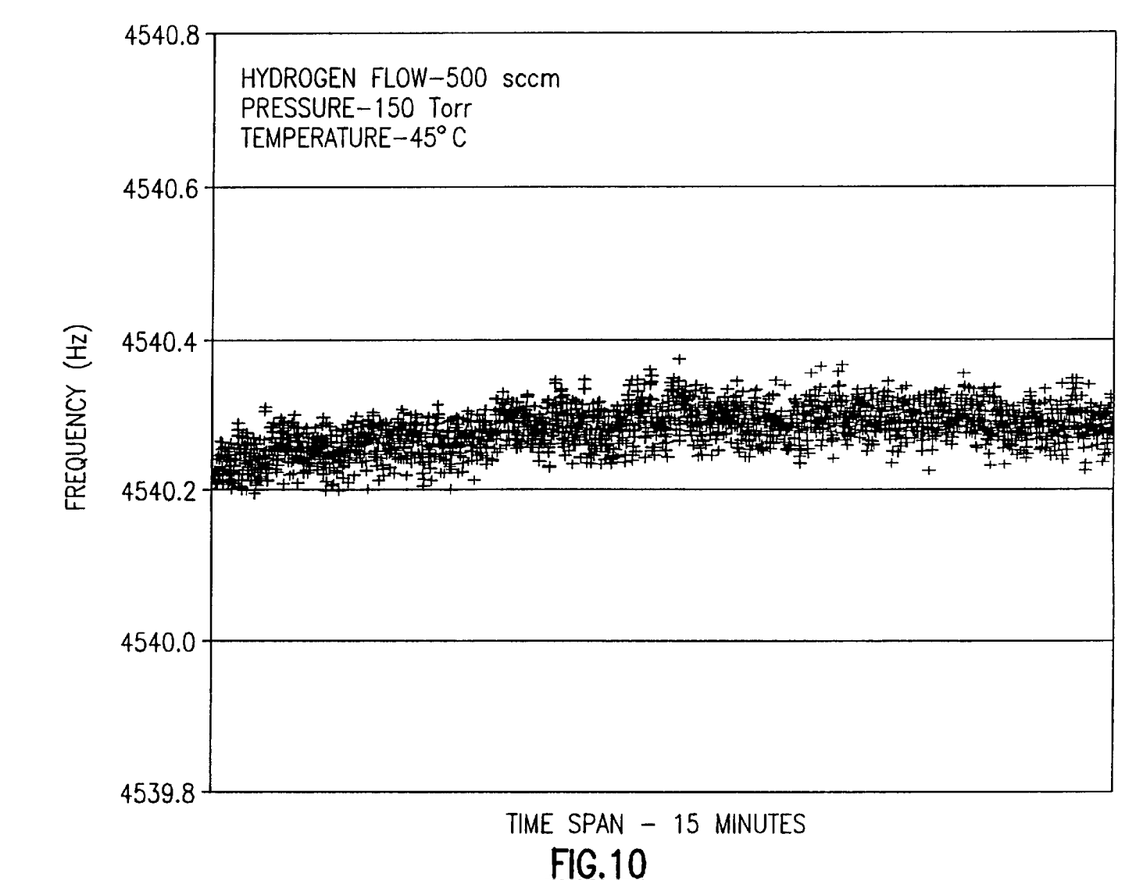
FIG. 10 shows a scatter plot of measured resonance frequencies in hydrogen gas at 45° C.

FIG. 10 shows a scatter plot of measured resonance frequencies in hydrogen gas tested at a flow rate of 500 sccm at 45° C. and 150 Torr. The measurement time is 200 ms. As is evident from FIG. 10, the range of scatter is about 0.2 Hz over a period of fifteen minutes, revealing a short term temperature stability on the order of 0.05° C. This translates into an accuracy of 0.0045% in frequency readout or equivalently 0.00011% of TMI in hydrogen gas.

Figure 11:
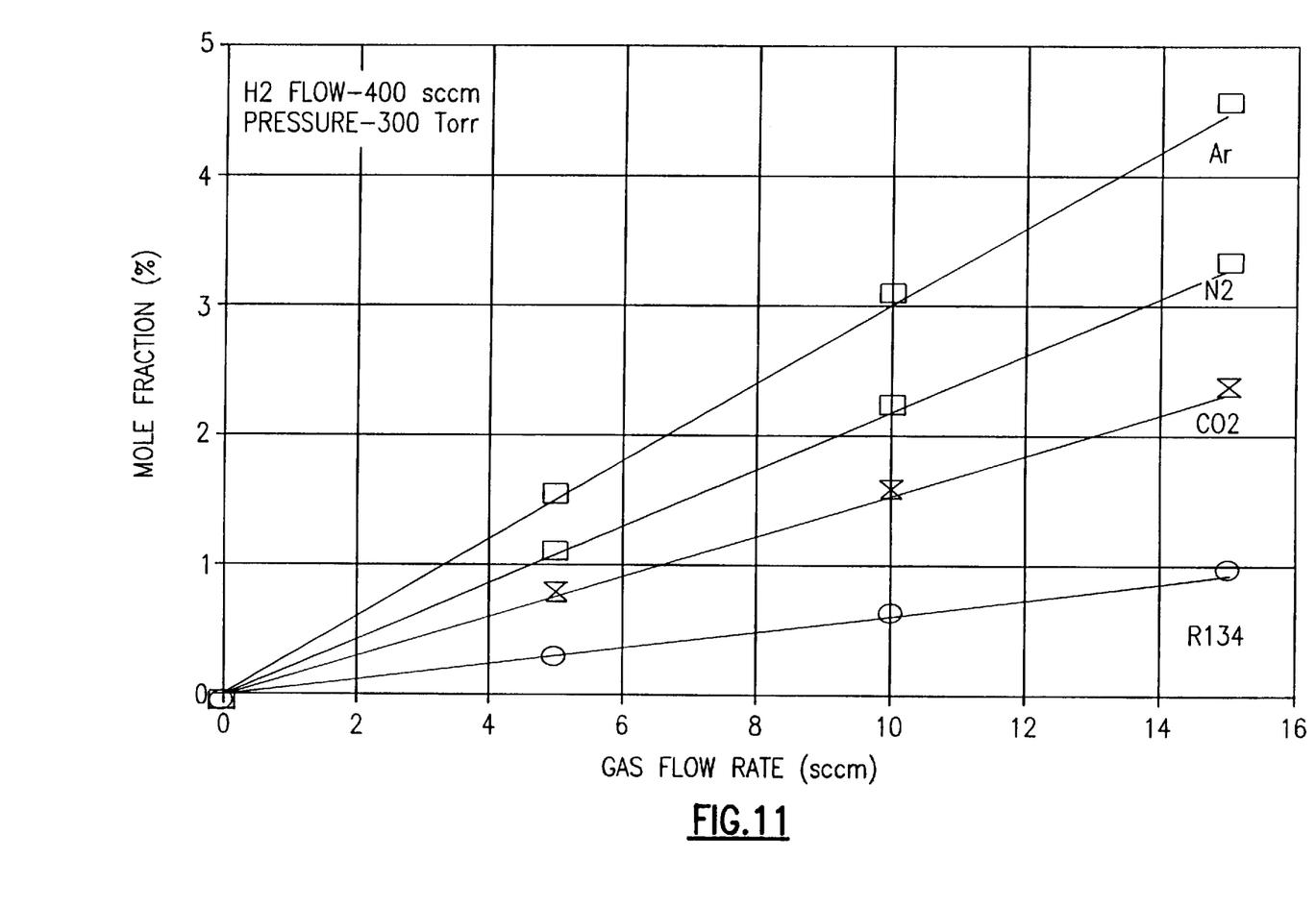
FIG. 11 shows mole fractions of Ar, $N_2$, $CO_2$, and R134a gasses in hydrogen gas plotted against gas flow rates.

Referring to FIG. 11, quantitative testing was performed using a variety of gasses in hydrogen primary gas. A mass flow controller (MFC) for each gas was carefully calibrated by recording the time required to fill a known volume, about 500 cc, through a fixed pressure increment, 500 Torr, to set a nominal mass flow rate. For nitrogen gas, the calibration factor varied between 0.99 to 1.02. For hydrogen gas, the calibration factor varied between 1.09 to 1.15. For argon, carbon dioxide, and R134a gasses, the calibration factor was 1.36, 0.70, and 0.28 respectively. These gas calibration factors, specific to each MFC, were used to estimate the mole fraction of the flow gasses in the primary hydrogen gas. The mole fraction estimates for argon, nitrogen, carbon dioxide, and R134a gas in hydrogen are shown in FIG. 10 plotted against gas flow rates as straight lines. The primary hydrogen gas flow was fixed at 400 sccm at 300 Torr.

At the same time, resonance frequencies of the acoustic cell were measured in the same gas flow at gas flow rates of 5, 10 and 15 sccm. The results are shown in FIG. 11 as discrete data points based on measured frequencies. The mole fractions measured with the acoustic cell of the present invention are very close to the estimates from the calibrated MFC's. The maximum frequency shift in this set of data was 1017 Hz, which is equivalent to 0.63% of TMI in hydrogen.

Figure 12:
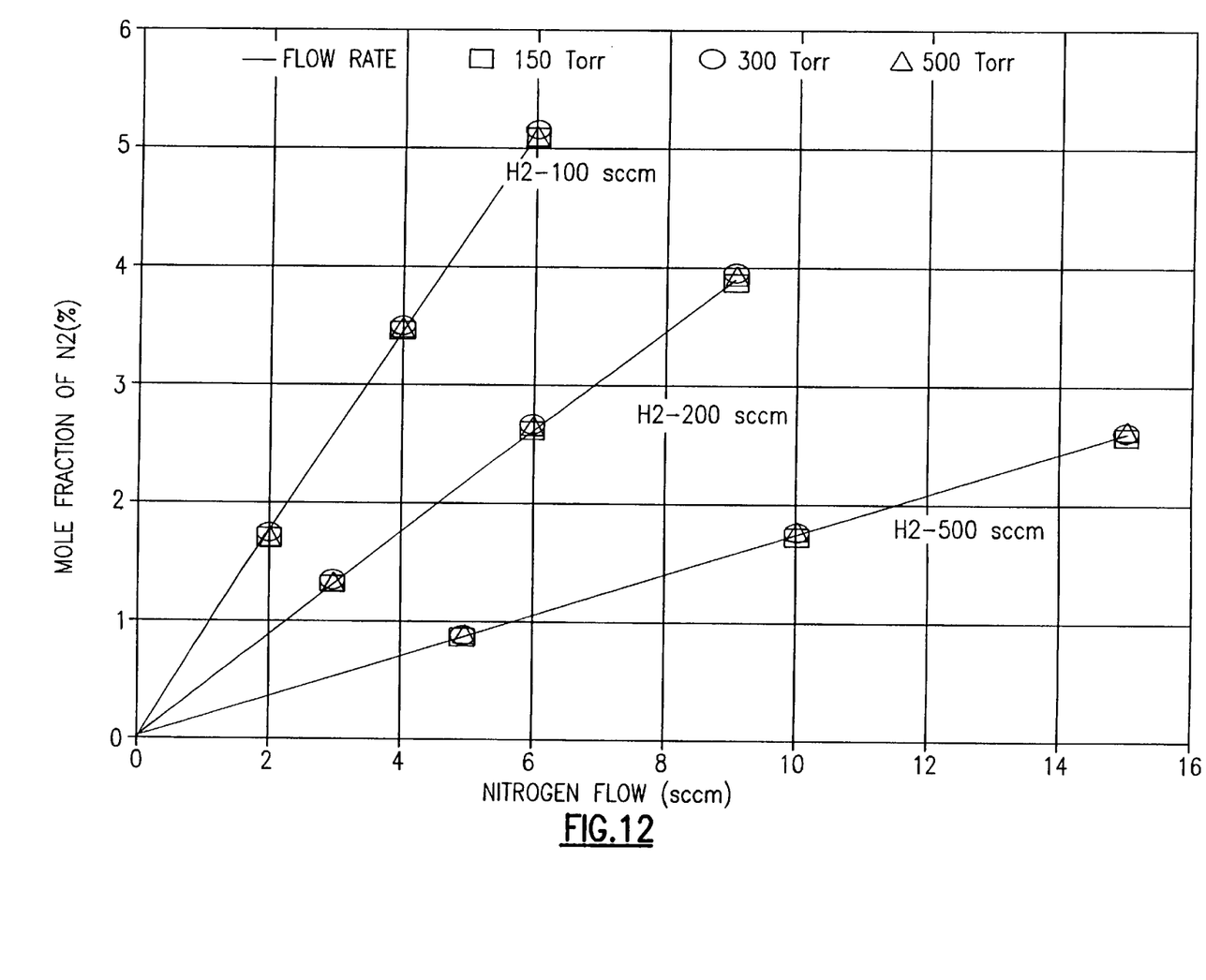
FIG. 12 shows the mole fraction of $N_2$ in hydrogen gas plotted against $N_2$ flow rates.

Referring to FIG. 12, the right lines show the estimates of nitrogen mole fraction as the flow rate is varied at different operating pressures. The discrete data points are from frequency measurements using the acoustic cell of the present invention at various pressures. FIGS. 11 and 12 demonstrate high quantitative accuracy of the present invention at a wide range of operating pressures and flow rates in a variety of gasses.

Figure 13:
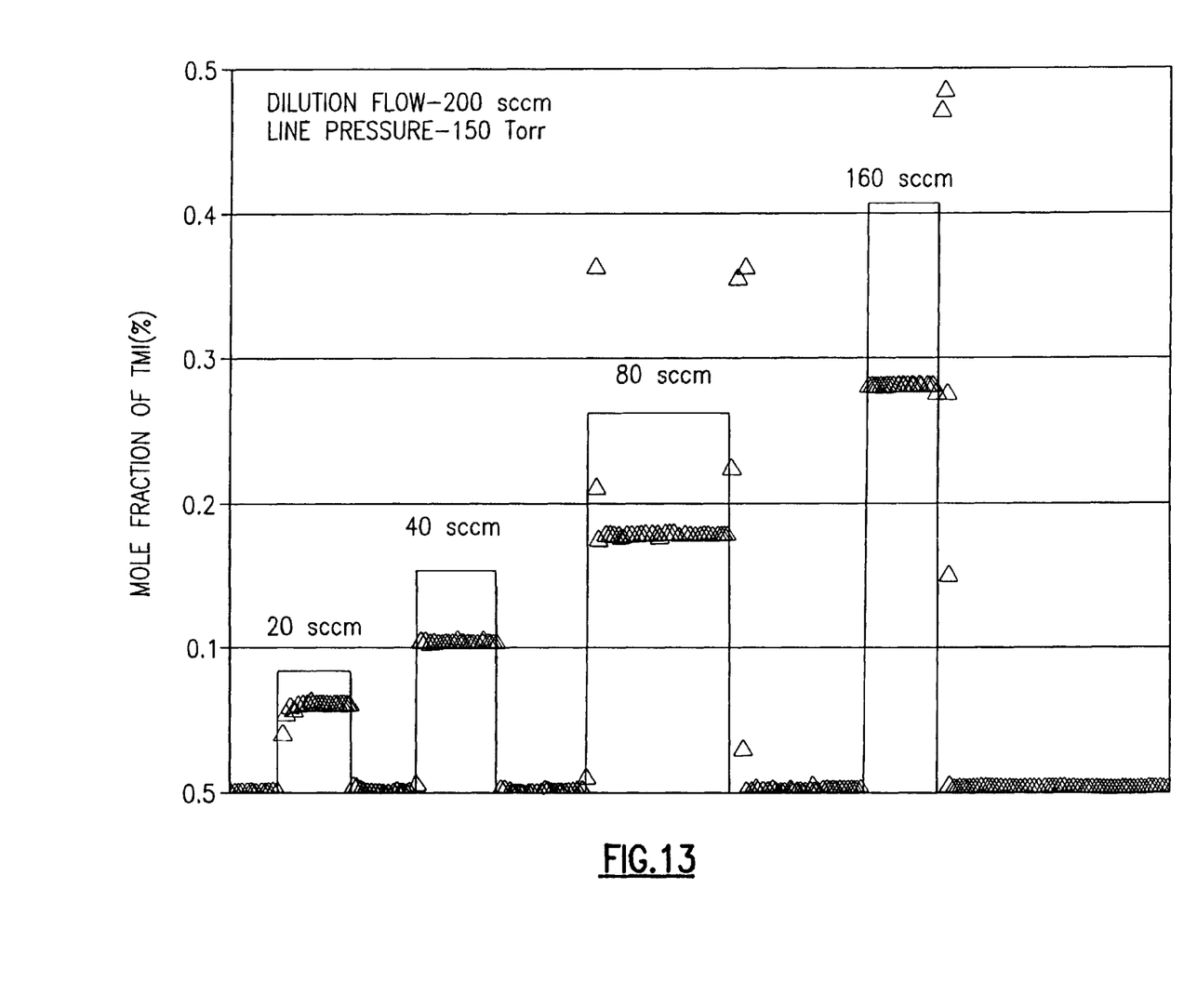
FIG. 13 shows the mole fraction of TMI indicated by the present invention with step changes in the TMI bubbler flow rate.

Referring to FIG. 13, the acoustic cell of the present invention was installed in the TMI line of an MOCVD reactor. The sample data is shown from a test in which the hydrogen flow through a TMI bubbler is varied. The solid line is based on calculations assuming steady state hydrogen gas flow through the bubbler and ideal TMI vapor pressure. The mole fraction as measured by the acoustic cell of the present invention is plotted as discrete data points. The operating pressure was 150 Torr and 200 sccm of hydrogen gas was added for dilution.

The discrepancy between the measured mole fraction and the estimated ideal mole fraction increases as the bubbler rate flow increases. It is believed that the TMI pickup efficiency decreases at higher hydrogen flow rates through the TMI bubbler. Thus, conventional methods for calculating mole fraction on the basis of mass flow rates are likely to be overestimated.

Figure 14:
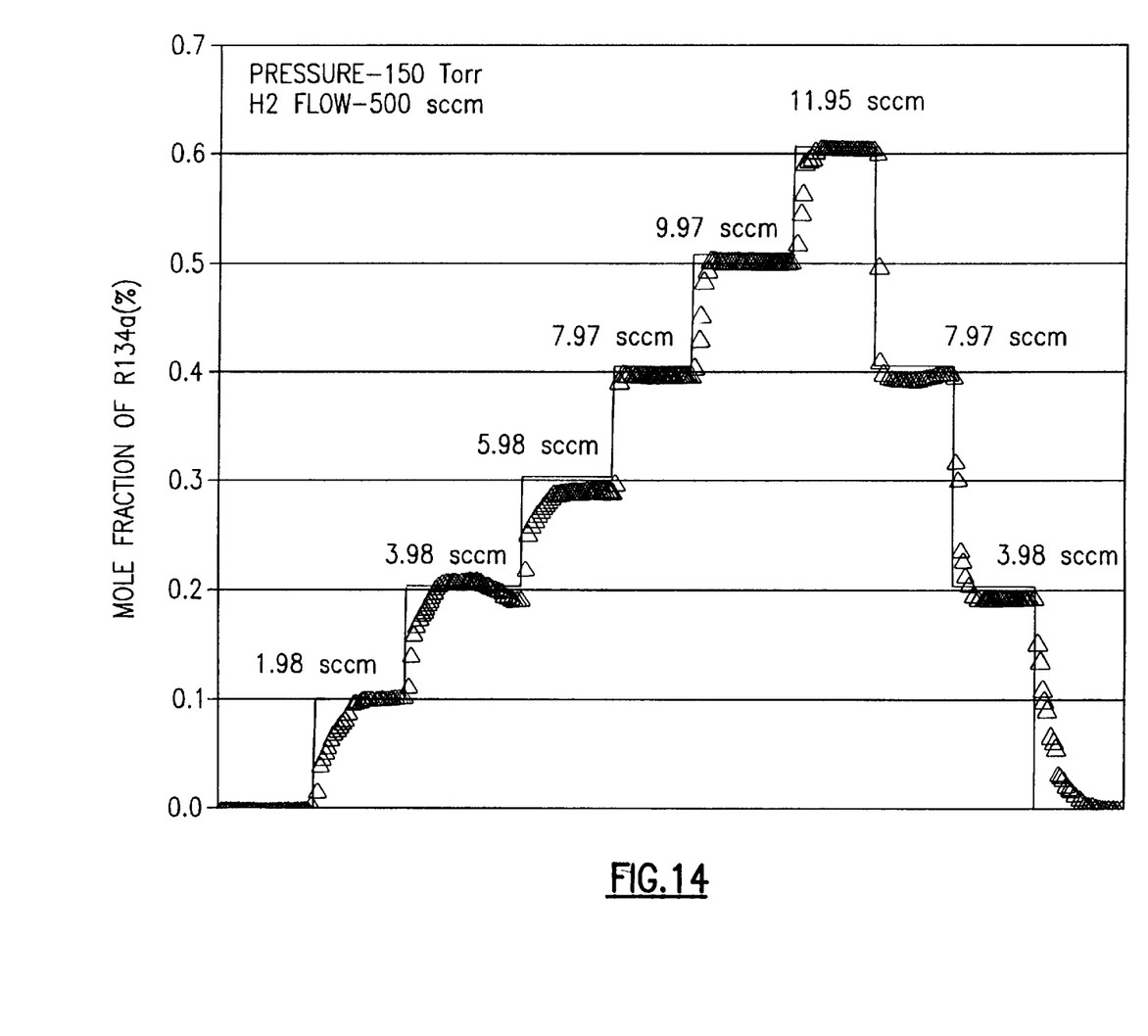
FIG. 14 shows the mole fraction of R134a gas in hydrogen gas indicated by the present invention with step changes in the R134a gas flow rate.

Referring to FIG. 14, similar testing was done using R134a gas. The solid line is based on a calibrated mass flow controller, whereas the discrete data points are the result of measurements made with the present invention. There is excellent quantitative agreement between the acoustic cell and the calibrated mass flow controllers.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

We claim:

1. An acoustic cell for analyzing the gas concentration of a gas flowing gas mixture, said cell comprising:

a cell housing;

said cell housing including an interior having a plurality of adjacently coupled acoustic cavities which defines a resonator chamber;

gas flowing means, fluidly connected to said cell housing, for flowing a gas mixture through said resonator chamber;

acoustic driving means at a first end of said cell housing for sending an acoustic signal through said gas mixture flowing through said cell housing;

receiving means at a second end of said cell housing for receiving said acoustic signal;

processing means for processing said received acoustic signal;

means for detecting the resonant frequency of said flowing gas mixture; and for determining the composition of said gas mixture, and means for acoustically isolating at least one of said driving means and said receiving means from said cell.

2. An acoustic cell according to claim 1, wherein said flowing means includes:

a gas inlet tube connected to said housing by a gas inlet in said cell housing; and a gas outlet tube connected to said cell housing by a gas outlet in said cell housing.

3. An acoustic cell according to claim 1, wherein a number of said plurality of acoustic cavities is three.

4. An acoustic cell according to claim 1, wherein at least two of said plurality of acoustic cavities are of different size.

5. An acoustic cell according to claim 1, wherein said driving means includes:
a driver transducer; and
a first diaphragm between said driver transducer and said first end of said cell housing.

6. An acoustic cell according to claim 5, wherein said driver transducer includes:
a driver cartridge housing;
a metal housing fitting inside said driver cartridge housing;
at least one acoustically isolating o-ring around said driver cartridge housing;
at least one acoustically isolating o-ring inside said driver cartridge housing;
a driving microphone inside said metal housing adjacent said first diaphragm;
an anti-driving microphone inside said metal housing back to back with said driving microphone; and
said driving microphone and said anti-driving microphone sharing a synchronous input.

7. An acoustic cell according to claim 6, wherein said receiving means includes:
a receiver transducer; and
a second diaphragm between said receiver transducer and said second end of said cell housing.

8. An acoustic cell according to claim 7, wherein said receiver transducer includes:
a receiver cartridge housing;
at least one acoustically isolating o-ring around said receiver cartridge housing; and
a receiver microphone inside said receiver cartridge housing adjacent said second diaphragm.

9. An acoustic cell according to claim 8, wherein:
said driving microphone and said anti-driving microphone are electrodynamic microphones; and
said receiver microphone is an electret microphone.

10. An acoustic cell according to claim 1, wherein:
said driving means includes an electrostatic microphone; and
said receiver means includes a capacitance microphone.

11. An acoustic cell according to claim 1, wherein:
said driving means includes a driver cartridge housing;
at least one acoustically isolating o-ring around said driver cartridge housing;
a first diaphragm between said driver cartridge housing and said first end of said cell housing;
a metal housing fitting inside said driver cartridge housing;
a driving microphone inside said metal housing adjacent said first diaphragm;
an anti-driving microphone inside said metal housing in a back to back relationship with said driving microphone;
said driving microphone and said anti-driving microphone sharing a synchronous input; and
said receiver means includes
a receiver cartridge housing;
a second diaphragm between said receiver cartridge housing and said second end of said housing;
at least one acoustically isolating o-ring around said receiver cartridge housing; and
a receiver microphone inside said receiver cartridge housing adjacent said second diaphragm.

12. An acoustic cell according to claim 11, wherein an operating frequency of said acoustic cell is lower than both a self-resonance frequency of said first diaphragm and a self-resonance frequency of said second diaphragm.

13. An acoustic cell according to claim 11, wherein an operating frequency of said acoustic cell is lower than both a self-resonance frequency of said driver cartridge housing and a self-resonance frequency of said receiver cartridge housing.

14. An acoustic cell according to claim 11, further comprising:
heating means, attached to said cell housing, for heating said acoustic cell; and
sensing means, attached to said cell housing, for sensing a temperature of said acoustic cell.

15. An acoustic cell according to claim 1, further comprising:
heating means, attached to said cell housing, for heating said acoustic cell; and
sensing means, attached to said cell housing, for sensing a temperature of said acoustic cell.

16. An acoustic sensor for analyzing the gas composition of a flowing gas mixture, said sensor comprising:
a housing;
said housing including an interior having a plurality of acoustic cavities defining a resonator chamber;
flowing means, fluidly connected to said housing, for flowing a gas mixture through said housing;
driver transducing means at a first end of said housing for receiving a driving electrical signal, converting said driving electrical signal to a driving acoustic signal, and sending said driving acoustic signal through said resonator chamber;
receiver transducing means at a second end of said housing for receiving a received acoustic signal, converting said received acoustic signal to a received electrical signal, and outputting said received electrical signal;
means for acoustically isolating at least one of said driver transducing means and said receiver transducing means from the remainder of the sensor;
processing means for sending said driving electrical signal to said driver transducing means and for receiving said received electrical signal outputted by said receiver transducing means;
means for varying a frequency of said driving acoustic signal; and
means for detecting a resonance frequency associated with said gas mixture;
wherein said processing means includes means for determining a composition of said gas mixture.

17. An acoustic sensor according to claim 16, wherein said means for detecting a resonance frequency associated with said gas includes measuring a phase lag of said received electrical signal with respect to said driving electrical signal.

18. An acoustic sensor according to claim 16, wherein said means for detecting a resonance frequency associated with said gas includes measuring an amplitude of said received electrical signal with respect to said driving electrical signal.

19. An acoustic sensor according to claim 16, including means for monitoring and controlling the temperature within said resonant chamber.

20. An acoustic sensor according to claim 16, including three adjacent acoustic cavities disposed between said driver transducing means and said receiver transducer means defining an acoustic resonance chamber, in which first and second acoustic cavities of substantially the same size sandwich a third smaller acoustic cavity, said acoustic resonance chamber having a total volume which is less smaller than 20 cc.

21. An acoustic sensor according to claim 20, wherein the sensor has an operating frequency which is less than approximately 5 kilohertz.

22. A method for determining the composition of a gas mixture, said method comprising the steps of:

provide an acoustic cell having a plurality of acoustic cavities;

flowing a gas mixture through said acoustic cell;

receiving a driving electrical signal from a digital signal controller;

converting said driving electrical signal to a driving acoustic signal;

sending said driving acoustic signal through said gas mixture flowing through said acoustic cell from driving means provided in said acoustic cell;

receiving, using receiving means disposed in an opposite end of said cell, a received acoustic signal after the step of sending said driving signal through said gas mixture;

acoustically isolating at least one of the sending means and receiving means from the remainder of said cell prior to sending said acoustic signal;

converting said received acoustic signal to a received electrical signal;

outputting said received electrical signal to said digital signal controller;

processing, within said digital signal controller, said received electrical signal to detect a resonance frequency associated with said gas mixture; and determining, based on said resonance frequency, the composition of said gas mixture.

\* \* \* \* \*